US00PP16548P3

(12) United States Plant Patent
Danziger

(10) Patent No.: US PP16,548 P3
(45) Date of Patent: May 16, 2006

(54) *PETUNIA* PLANT NAMED 'DANDOPINK'

(50) Latin Name: *Petunia hybrida*
Varietal Denomination: Dandopink

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 63 days.

(21) Appl. No.: 10/930,772

(22) Filed: Sep. 1, 2004

(65) Prior Publication Data

US 2006/0048256 P1 Mar. 2, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Anne Marie Grunberg
(74) *Attorney, Agent, or Firm*—Foley & Lardner LLP

(57) ABSTRACT

A new and distinct *Petunia* plant named 'Dandopink' characterized by the combined characteristics of pink flowers, RHS 74B; double flower type, 3 cm flower diameter; vigorous growth habit, developing into a rounded, trailing plant in 3 months; flowers in early summer and stays in full bloom season long; performs well in the garden; and suitable for patios as hanging baskets, and outdoors bedding.

2 Drawing Sheets

Latin name of the genus and species of the claimed plant: *Petunia hybrida.*
Variety denomination: Dandopink.

BACKGROUND OF THE INVENTION

The present invention relates to a new and distinct cultivar of *Petunia* plant, botanically known as *Petunia hybrida,* hereinafter referred to by the cultivar name 'Dandopink'.

The new cultivar originated from cross made in a controlled breeding program in Moshav Mishmar Hashiva, Israel. The female parent is a *Petunia* variety designated 'DP200' (unpatented). The male parent is a *Petunia* variety of designated 'VD100' (unpatented). 'Dandopink' was discovered and selected by the inventor, Gabriel Danziger, as a flowering plant within the progeny of the stated cross in a controlled environment in Moshav Mishmar Hashiva, Israel.

Asexual reproduction of the new cultivar by cutting of side shoots, was first performed October, 2001 in Moshav Mishmar Hashiva, Israel and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be basic characteristics of 'Dandopink' which in combination distinguish this *Petunia* as a new and distinct cultivar.

1. Pink flowers, RHS 74B; double flower type, 3 cm flower diameter
2. Vigorous growth habit, developing into a rounded, trailing plant in 3 months;
3. Flowers in early summer and stays in full bloom season long;

4. Performs well in the garden; and
5. Suitable for patios as hanging baskets, and outdoors bedding.

Table 1 provides a comparison among plants of 'Dandopink' and plants of the parents, 'DP200' (female parent, unpatented) and 'VD-100' (male parent, unpatented):

| Characteristic | 'Dandopink' | 'DP200' (female parent, unpatented) | 'VD100' (male parent, unpatented) |
|---|---|---|---|
| Petal color | Pink | Pink | Pink |
| Growth habit | Trailing | Trailing | Trailing |
| Flower Diameter | 1.8 inches | 2 inches | 1 inches |

Of the many commercial cultivars known to the inventor, the most similar in comparison to 'Dandopink' is the *Petunia* cultivar 'Doubloon Pink'.

| Characteristic | 'Dandopink' | 'Doubloon Pink' |
|---|---|---|
| Petal color | Pink, RHS 74 B | Rose pink |
| Growth habit | Mound | Spreading |
| Flower Diameter | 3 cm | 4 cm |

'Dandopink' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions, which closely approximate those generally used in commercial practice.

BRIEF DESCRIPTION OF THE DRAWING

The accompanying photographic drawings illustrate the overall appearance of the new *Petunia* showing the colors as true as is reasonably possible with colored reproductions of this type.

The first photograph shows a close-up of a single flower of a 3 month old 'Dandopink' plant.

The second photograph shows a flowering 3 month old 'Dandopink' plant in a hanging pot.

DETAILED BOTANICAL DESCRIPTION

The following observations, measurements and values describe the new cultivar as grown in Moshav Mishmar Hashiva, Israel under conditions which closely approximate those generally used in commercial practice. 'Dandopink' can be used as a pot and bedding plant. For optimal growth, 'Dandopink' should be grown outdoors in moderate climate, in full sunlight, and indoors during winter. Irrigation and fertilization are recommended on a regular basis. A fully grown plant takes 3 months.

Color references are made to The Royal Horticultural Society Colour Chart (R.H.S.) 2001, except where general colors of ordinary significance are used. Color values were taken under daylight conditions at approximately noon in Moshav Mishmar Hashiva, Israel. The age of the plant described is 3 months.

Plant:

General appearance and form:

*Height.*—8–10 inches. Spread: 25–30 inches.

*Growth habit.*—Mound.

*Growth rate.*—Fully grown plant in 3 month.

*Branching habit and description.*—Freely.

*Flowering response.*—Long day.

*Flowering season.*—Summer and autumn.

*Winter hardiness/weather tolerance.*—Frost tender; plants may be damaged by temperatures below 5° C.

*Lastingness of the individual bloom.*—4–6 days.

*Time to initiate roots.*—1 week.

*Time to produce a rooted cutting.*—2–3 weeks.

*Fragrance.*—None.

Stem description:

*Length.*—10–15 inches.

*Diameter.*—0.2 inch.

*Internode length and color.*—1 inch, Yellow-Green 144A.

*Strength.*—Medium.

Branching: Freely.

Pubescence: Yes.

Foliage:

*Overall shape of leaf.*—Elliptic.

*Arrangement.*—Alternate.

*Apex.*—Acute.

*Base.*—Obtuse.

*Length.*—3 inches.

*Width.*—1.25 inches.

*Margin.*—Entire.

*Texture.*—Lustrous.

*Color of upper surface.*—Mature leaf: Yellow-Green 146 A. Immature leaf: Yellow-Green 146 A.

*Color of lower surface.*—Mature leaf: Yellow-Green 146 B. Immature leaf: Yellow-Green 146 B.

*Venation color.*—Upper surface: Yellow-Green 144D. Lower surface: Yellow-Green 144D.

*Petiole.*—Length: 0.5 inch. Diameter: 0.2 inch. Color: Yellow-Green 146D.

Inflorescence:

*Flower longevity.*—About —4–6 days.

*Flower size (diameter).*—1.3 inches.

*Flower type.*—Double flower.

*Average number of flowers per lateral branch.*—4–6.

*Petals.*—Number: Average 10. Shape: Double flower. Size: Length: About 1.2 inches; width: About 1.2 inches. Apex: Cuspidate. Margin: Entire. Texture: Glabrous. Color: Pink. Upper surface: Red-Purple group RHS 74B. Lower surface: Red-Purple group RHS 69C.

*Sepals.*—Number: 5. Shape: Elliptic. Size: Length 0.4 inch width 0.1 inch. Apex: Obtuse. Margin: Entire. Texture: Lustrous. Color: Upper surface: Green 137 B. Lower surface: Green 137 B.

*Bud.*—Rate of opening: 7–10 days. Color: Green 141 D. Shape: Flanged. Length: 0.7 inch. Diameter: 0.3 inch. Peduncle color and length: Green 141 C; 0.6 inch.

Reproductive organs:

*Stamen.*—5 in number fused to petals; color white 155 A.

*Anthers.*—White 155 A.

*Filament.*—Yellow-Green 142 B.

*Stigma.*—Yellow-Green 146 C.

*Ovary.*—Yellow-Green 146 C.

*Pollen.*—White 155 A.

Seed:

*Number.*—15–20.

*Width.*—0.04 inch.

*Length.*—0.04 inch.

*Shape.*—Ovoid.

*Color.*—Brown 200 C.

Fruit:

*Number.*—Few, when naturally pollinated.

*Width.*—0.12 inch.

*Length.*—0.24 inch.

*Shape.*—Ellipsoid.

*Color.*—Grew-Brown 199 A.

Disease/pest resistance/susceptibility: Unknown.

I claim:

1. A new and distinct *Petunia* plant named 'Dandopink', as illustrated and described herein.

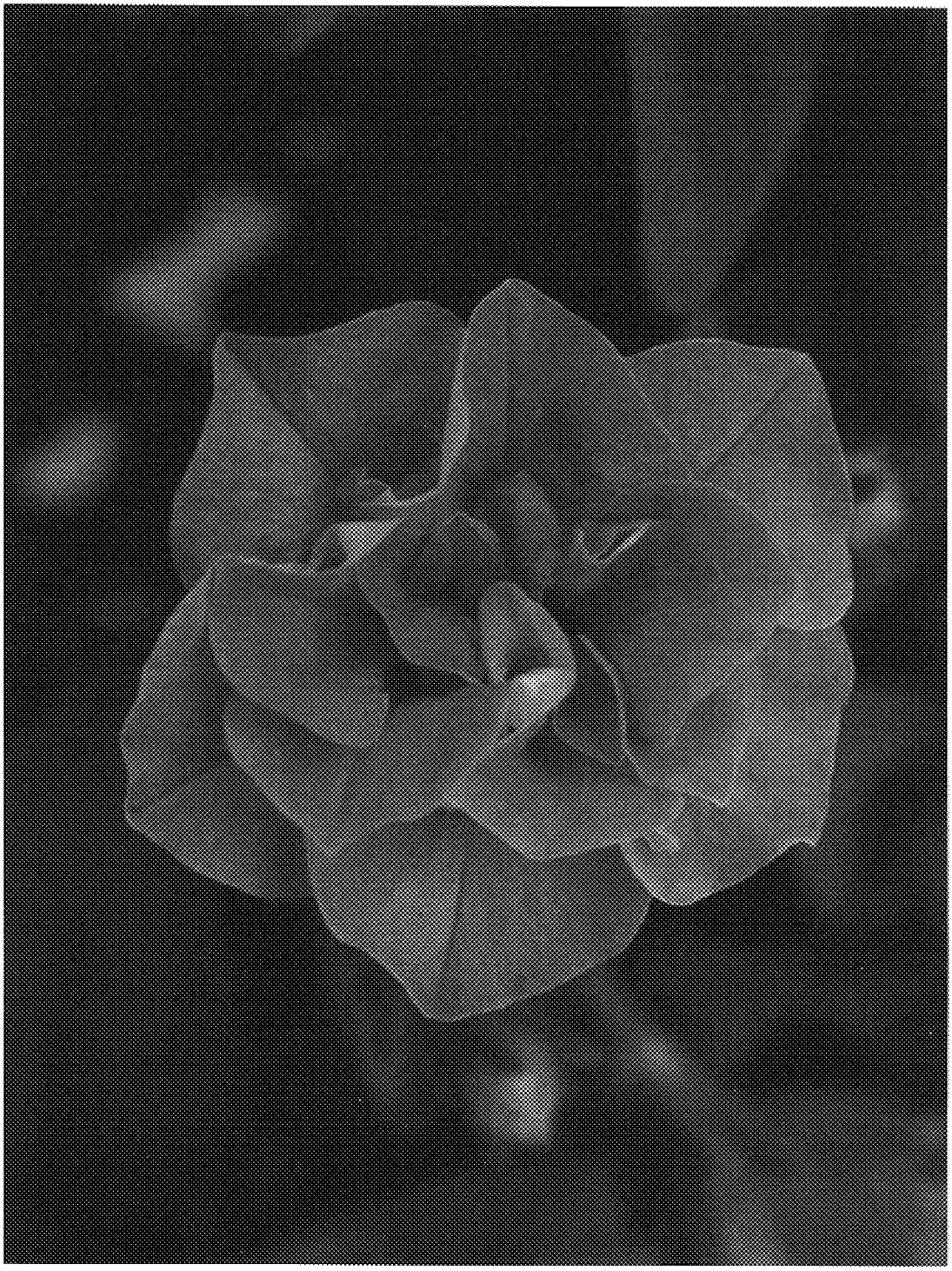

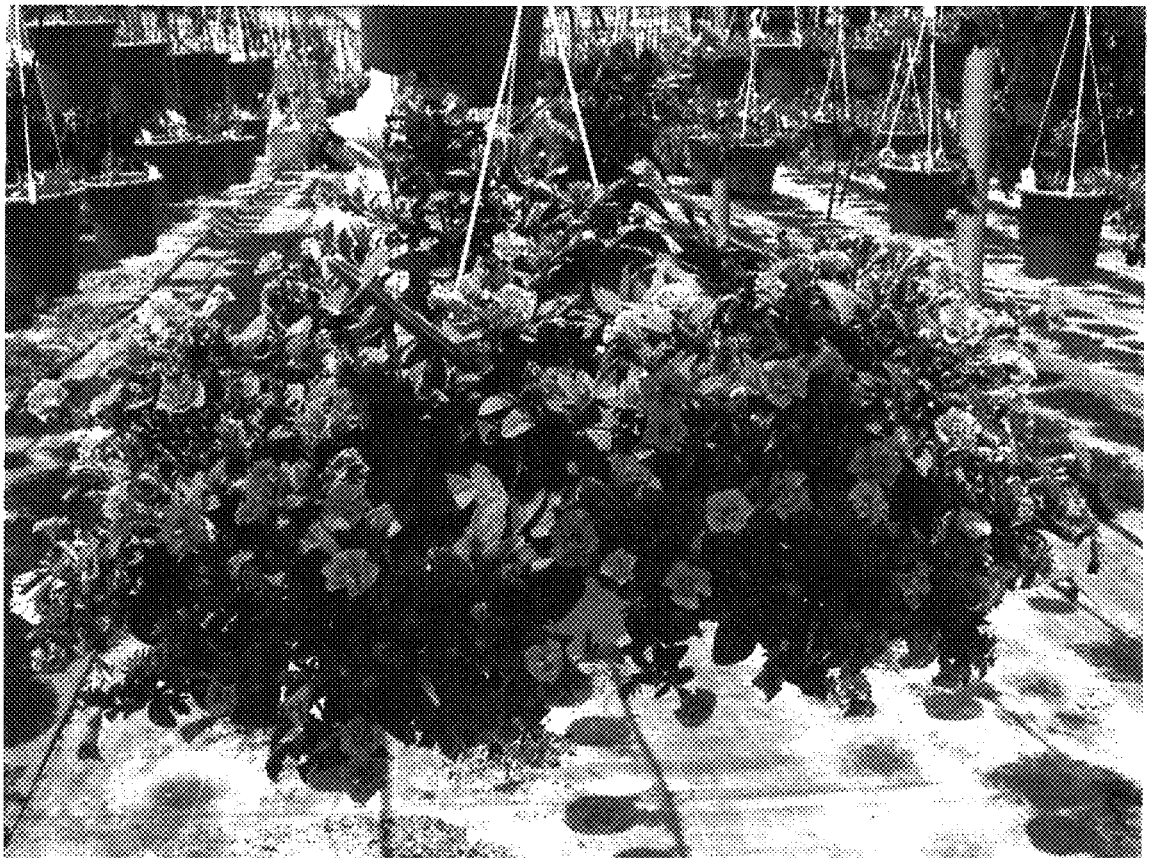

* * * * *